United States Patent [19]

Kitajima

[11] Patent Number: 5,184,634
[45] Date of Patent: Feb. 9, 1993

[54] CUP CLEANING APPARATUS
[75] Inventor: Masaichi Kitajima, Akigawa, Japan
[73] Assignee: Olympus Optical Co., Ltd., Tokyo, Japan
[21] Appl. No.: 746,247
[22] Filed: Aug. 15, 1991
[30] Foreign Application Priority Data
  Aug. 24, 1990 [JP] Japan .................. 2-223615
[51] Int. Cl.5 .............................................. B08B 9/08
[52] U.S. Cl. .................. 134/95.1; 134/166 R
[58] Field of Search ........... 134/95.1, 95, 102, 144, 134/152, 166 R, 167 R, 168 R, 171; 15/302, 304; 141/92

[56] References Cited

U.S. PATENT DOCUMENTS

| | | | |
|---|---|---|---|
| 1,854,471 | 4/1932 | Hofmann | 15/304 X |
| 2,309,290 | 1/1943 | Aksomitas | 15/304 X |
| 2,811,975 | 11/1957 | Tatibana | 134/102 |
| 3,120,237 | 2/1964 | Lang | 134/167 X |
| 3,849,830 | 11/1974 | Wagner | 15/304 X |
| 3,916,924 | 11/1975 | McGowan | 134/168 X |
| 4,406,298 | 9/1983 | Martin | 134/171 X |

FOREIGN PATENT DOCUMENTS

| | | | |
|---|---|---|---|
| 644975 | 10/1928 | France | 134/102 |
| 504646 | 12/1954 | Italy | 134/171 |

Primary Examiner—Philip R. Coe
Attorney, Agent, or Firm—Frishauf, Holtz, Goodman & Woodward

[57] ABSTRACT

An apparatus for cleaning a dilution cup used in a body fluid analyzer with which is performed an immunological examination such as an examination of infectious disease and determination of blood groups using urine, blood serum, blood cells and blood plasma, comprises a first inlet for cleaning water into a dilution cup, a second inlet for supplying air into the dilution cup, an outlet for discharging cleaning water and air in the dilution cup, and a sealing member for hermetically sealing the dilution cup.

5 Claims, 3 Drawing Sheets

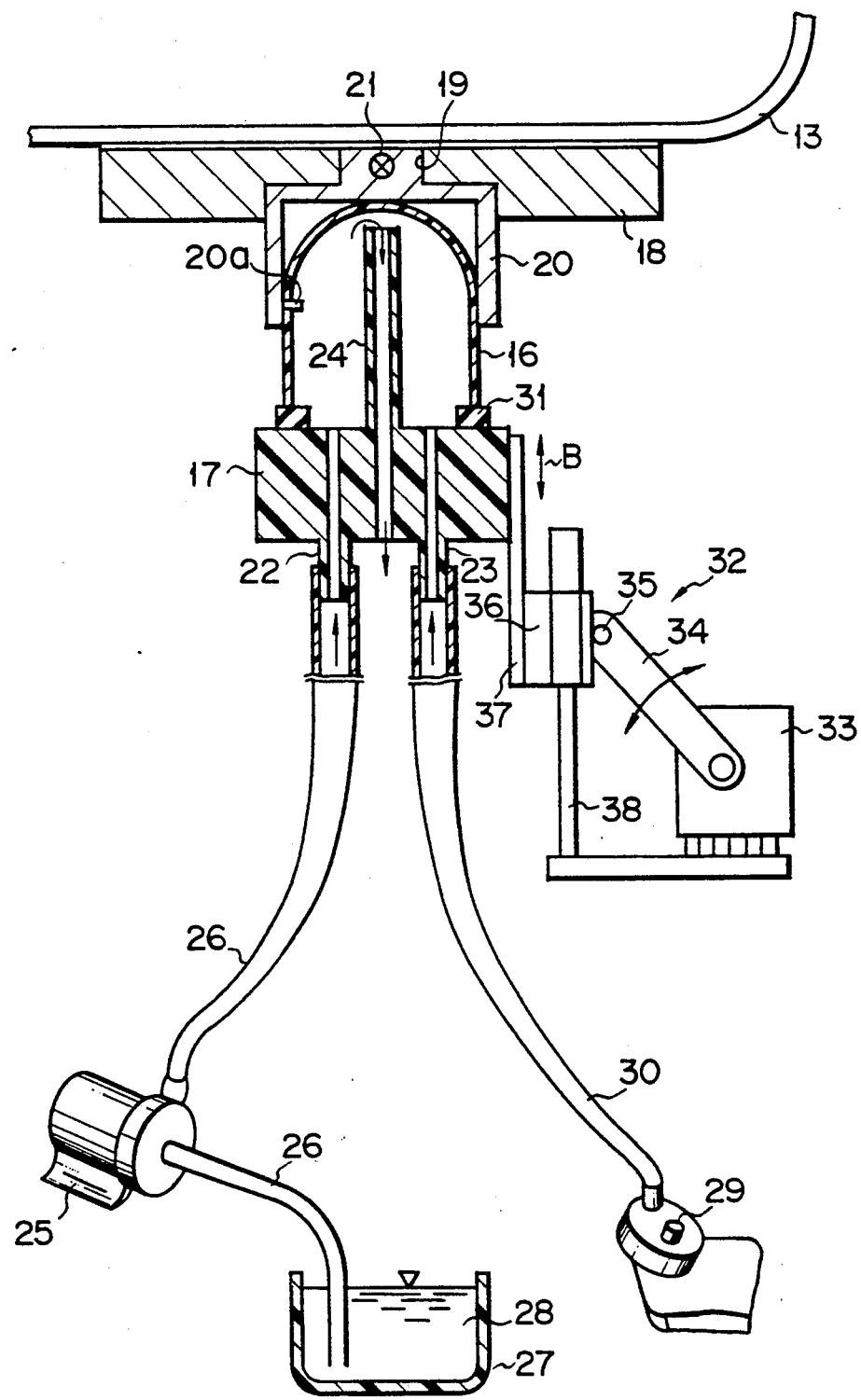
F I G. 1

CUP CLEANING APPARATUS

BACKGROUND OF THE INVENTION

1. Field of the Invention

This invention relates to an apparatus for cleaning a cup used in a body fluid analyzer.

2. Description of the Related Art

Dilution cups used in an automatic body fluid analyzer for analyzing a body fluid such as blood or urine are automatically cleaned to prevent carry-over before dilution of samples of the next step.

In a conventional method, cleaning water 3 is supplied from a cleaning water supply nozzle 2 into a dilution cup 1, as shown in FIG. 4(A), and the cleaning water is discharged from the cup 1 through a discharging nozzle 4, as shown in FIG. 4(B). These steps are repeated several times.

In another conventional method, cleaning water 3 is continuously supplied to a dilution cup 1 fully sealed by a packing 5 so as to clean the cup 1, as shown in FIG. 5.

Cleaning water must be increased to reduce carry-over. As a result, the capability of cleaning the cup 1 is adversely lowered. Further, when cleaning water is mixed with a detergent which can easily clean dirt, carry-over can remarkably be reduced. Further, when such a detergent is used, there is such an adverse effect that the detergent may react on a sample to be analyzed.

SUMMARY OF THE INVENTION

The object of this invention is to provide a cup cleaning apparatus which effectively reduces carry-over without using any detergent and without increasing the amount of cleaning water and cleaning time.

According to this invention, there is provided an apparatus for cleaning a dilution cup used in a body fluid analyzer with which is performed an immunological examination for a body fluid such as an examination of infectious disease and determination of blood groups using urine, and blood serum, blood cells and blood plasma, comprising a first inlet for supplying cleaning water into a dilution cup, a second inlet for supplying air into the dilution cup, an outlet for discharging water and air from the dilution cup, and a sealing member for hermetically sealing the dilution cup.

In this invention, a dilution cup may be cleaned at a position $P_4$ with its opening directed downward, at a position $P_5$ with the opening directed upward, or at both the positions $P_4$ and $P_5$, as shown in FIG. 2.

Air bubbles are jetted into water filled in the dilution cup such that innumerable interfaces are formed between the cleaning water and the air bubbles. The interfaces are caused to repeatedly contact the inner wall (particularly, the hemispherical bottom) of he dilution cup innumerable times or air in cleaning water is caused to hit against the inner wall of the dilution cup very strongly. When, therefore, the opening of the cup is directed downward, it is preferred that air is supplied from an air supply nozzle to the vicinity of the opening of the dilution cup and the tip of a discharging nozzle is disposed in the vicinity of the bottom of the dilution cup, as shown in FIG. 1. On the other hand, when the opening is directed upward, it is preferred that air is supplied from the air supply nozzle to the vicinity of the bottom of the dilution cup and the tip of the discharging nozzle is disposed in the vicinity of the bottom of the dilution cup, as shown in FIG. 3.

The dilution cup, a stem body, and first and second tubes may be made of any material that is not corroded by cleaning water and a sample liquid. More specifically, the cup may be made of vinyl chloride resin. Further, the stem body may be made of stainless steel or the like.

Additional objects and advantages of the invention will be set forth in the description which follows, and in part will be obvious from the description, or may be learned by practice of the invention. The objects and advantages of the invention may be realized and obtained particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 1 shows a cup cleaning apparatus according to this invention;

DETAILED DESCRIPTION OF THE PREFERRED EMBODIMENTS

An embodiment according to this invention will now be explained with reference to FIGS. 1 and 2.

Figure 2:
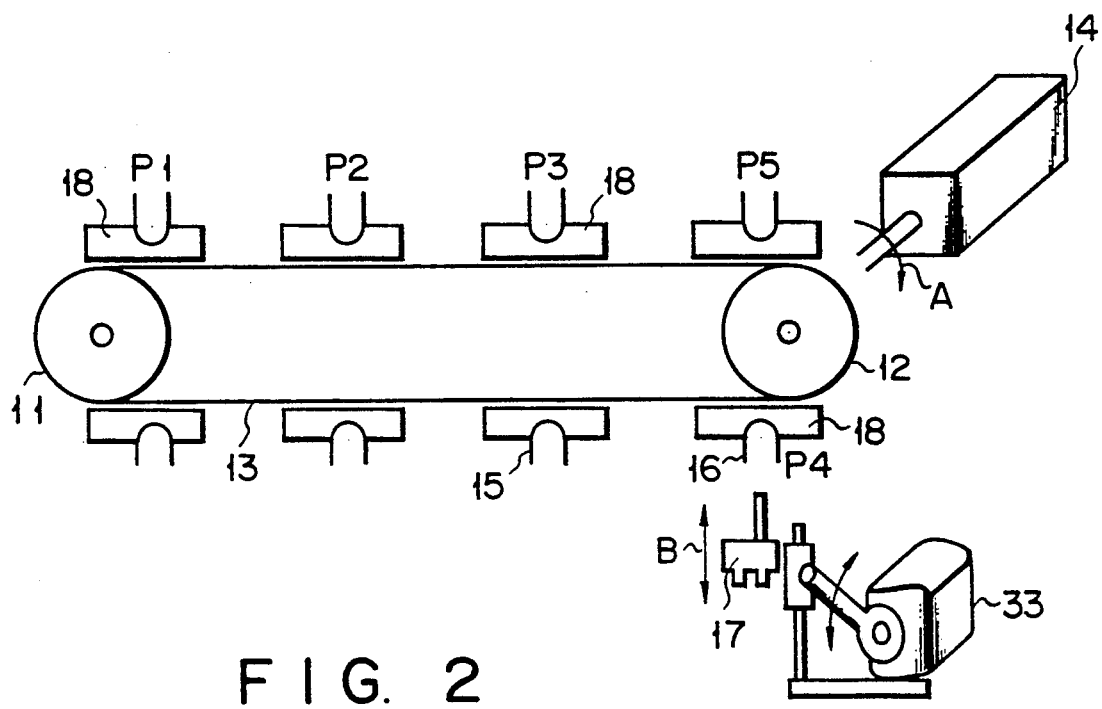
FIG. 2 is a view showing how to clean a dilution cup used in an automatic blood analyzer according to this invention.

FIG. 2 shows how to clean dilution cups used in an automatic blood analyzer according to this invention.

A timing belt 13 is stretched between a pair of pulleys 11 and 12 such that its displacement does not occur when it is driven. A first motor 14 is connected to the pulley 12 and rotates the same clockwise (in the direction shown by an arrow A). A second motor 15 is provided close to the pulley 12 and vertically is adapted to move a nozzle body 17 made of vinyl chloride for cleaning a dilution cup 16 made of vinyl chloride.

Each of the dilution cups 16 dispenses a body fluid such as blood plasma, blood cells, blood serum or urine and makes a dilution sample. The dilution cups 16 are connected to the timing belt 13 by means of metallic station blocks 18 or the like so as to stop at a position $P_1$ at which samples are dispensed, at a position $P_2$ at which dilution water is dispensed, at a position $P_3$ at which a dilution sample is sucked in and at a position $P_4$ at which the dilution cup is cleaned. More specifically, as shown in FIG. 1, a stepped opening 19 is formed in the station block 18 and a cylindrical holder 20 is fixed to the opening 19 by means of a screw 21. A projection 20a extends from the inner wall of the holder 20 inwardly. When the dilution cup 16 is inserted deepest into the holder 20, the dilution cup 16 is fully fixed into the holder 20 by the elastic force of the projection 20a. The cups are positioned at $P_1$, $P_2$, $P_3$ and $P_4$ by the operation of the first motor 14.

FIG. 1 shows an apparatus for cleaning dilution cups according to this invention.

At the position P$_4$, the dilution cup 16 is fixed to the holder 20 of a station block 18, with the opening directed downward. A cleaning water supply nozzle (first inlet) 22 for supplying cleaning water into the dilution cup 16 and an air supply nozzle (second inlet) 23 for supplying air into the dilution cup 16 are provided on the undersurface of the nozzle body 17. A discharging nozzle (outlet) 24 for discharging cleaning water and air from the dilution cup 16 extends from the upper surface of the nozzle body 17 such that its tip is disposed at the vicinity of the hemispherical bottom of the dilution cup 16.

A pump 25 for supplying cleaning water is connected to a first tube 26 made of vinyl chloride. One end of the first tube 26 is connected to the cleaning water supply nozzle 22 and the other end thereof extends in cleaning water 28 in a tank 27 such that the cleaning water 28 is supplied into the dilution cup 16. An air supply pump 29 is connected to the air supply nozzle 23 by means of a second tube 30 made of vinyl chloride. A ring-shaped rubber packing 31 acting as a seal member for hermetically sealing the dilution cup is attached to the upper surface of the nozzle body 17 by an adhesive so as to be integral with the nozzle body 17 and abut against the edge of the dilution cup 16. However, it is not always necessary that the rubber packing 31 be made integral with the nozzle body.

The nozzle body 17 is moved up and down by means of a driving mechanism 32 which comprises a third motor 33, a slidable cam 34 driven by means of the rotation of the motor 33, a vertically slidable plate 36 having a bearing 35 in contact with the cam 34, a guide rod 38 connected to the nozzle body 17 by means of a connecting plate 37 for transmitting the driving force of the vertically slidable plate 36 in the vertical directions (in the directions of an arrow B). The vertically slidable plate 36 is moved up and down along the upright guide rod 38 in response to the rotational angle of the third motor 33. Since the apparatus is constructed as mentioned above, the vertically slidable plate 36 is lifted toward the dilution cup 16 which has been stopped at the position P$_4$ by controlling the rotational angle of the third motor 33 such that the nozzle body 17 is sealingly connected to the dilution cup 16. On the other hand, the vertically slidable plate 36 is moved downward by controlling the rotational angle of the third motor 33, whereby the nozzle 17 is separated from the dilution cup 16.

The operation of this embodiment will now be explained.

① After a sample has been dispensed, the dilution cup 16 at the position P$_1$ is moved to the position P$_2$ together with the timing belt 13 moved by the rotation of the first motor 14 and stops there.

② After a dilution liquid is dispensed from the dilution cup 16, the cup 16 is moved to the position Phd 3 at which a further dilution liquid is dispensed. Thereafter, a dilution sample is delivered from the dilution cup to the well of a reaction plate (not shown). Then, the dilution cup is moved to the position P$_4$ and stops there.

③ As the third motor 32 is rotated, the cam 34 swings and the vertically slidable plate 36 moves vertically along the guide rod 36. The rubber packing 31 mounted on the nozzle body 17 sealingly contacts the end face of the dilution cup 16.

④ The cleaning water 28 in the tank 27 is supplied by means of the pump 25 for supplying cleaning water from the cleaning water supply nozzle 22 into the dilution cup 16 through the first tube 26. Air is also supplied by the air supply pump 29 from the air supply nozzle 23 into the dilution cup 16 through the second tube 30. The cleaning water mixed with the air cleans the inner wall of the dilution cup 16, and is discharged from the discharging nozzle 24, which extends to the vicinity of the bottom of the dilution cup 16, to the outside of the dilution cup 16.

⑤ The cleaning water 28 enters in the dilution cup 16 from the end face of the dilution cup 16 (the outlet of the cleaning water supply nozzle) toward the bottom of the dilution cup 16 so as to be filled in the dilution cup 16 and is discharged from the discharging nozzle 24 at the vicinity of the bottom of the dilution cup 16. This process is continued. Simultaneously, air supplied from the vicinity of the end face of the dilution cup 16 enters the cleaning water filled in the dilution cup 16 in a form of bubbles, and innumerable interfaces are formed between the bubbles and the cleaning water. The interfaces repeatedly contact the inner wall of the dilution cup innumerable times or air introduced into the washing water strongly hits against the inner wall of the dilution cup, thereby enhancing the cleaning efficiency.

The cup cleaning apparatus according to the above-mentioned embodiment comprises a cleaning water supply nozzle 22 for supplying cleaning water 28 into a dilution cup 16, an air supply nozzle 23 for supplying air into the dilution cup 16, a discharging nozzle 24 for discharging cleaning water and air from the dilution cup 16, and a rubber packing 31 for hermetically sealing the dilution cup 16.

Accordingly, by supplying cleaning water 28 and air simultaneously into the dilution cup 16, the effect of cleaning the inner wall of the dilution cup 16 is enhanced without increasing the amount of cleaning water to be used and cleaning time. In the automatic blood analyzer, the number of reexamination for checking cup carry-over can be reduced.

Figure 3:
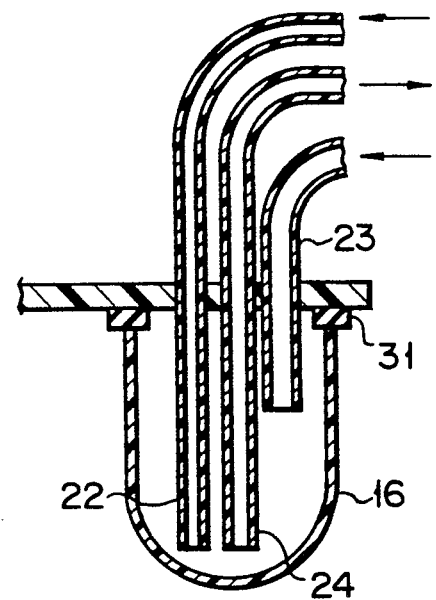
FIG. 3 is a cross-sectional view of the main part of another embodiment of the dilution cup.
Figure 4A:
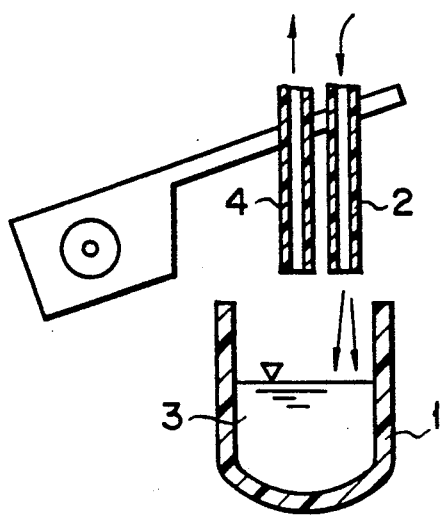
FIGS. 4(A) and 4(B) show how to supply cleaning water to the conventional dilution cup.
Figure 4B:
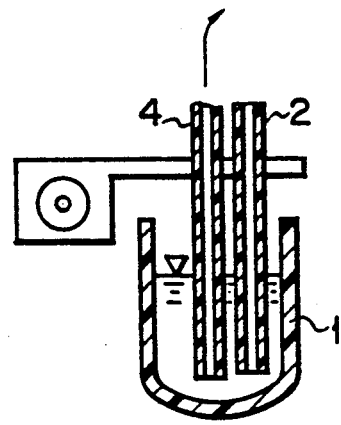
Figure 5:
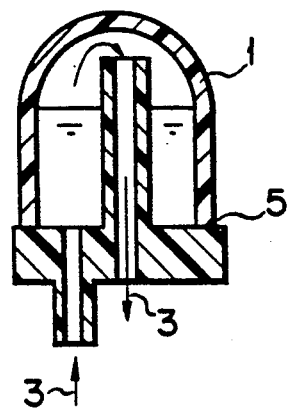
FIG. 5 shows how to continuously supply cleaning water to the conventional dilution cup.

In this invention, a dilution cup, a cleaning water supply nozzle, an air supply nozzle and a discharging nozzle can be arranged as shown in FIG. 3. In this case, for example, the dilution cup is set at the position P$_5$ which is disposed at the side opposite to the position P$_4$ in FIG. 2. Since the dilution cup 16 is set such that its opening is directed upward, the tips of the air supply nozzle 23 and the discharging nozzle 24 are disposed at the bottom of the dilution cup 16.

In place of the arrangement as shown in FIG. 1, the cup cleaning device according to this invention may be set at the position P$_4$ under the timing belt as shown in FIG. 1 and may be set at the position P$_5$ over the cleaning apparatus may be set at both the positions P$_4$ and P$_5$, the effect of cleaning the inner wall of the dilution cups is more increased.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An apparatus for cleaning a dilution cup used in a body fluid analyzer with which is performed an immunological examination such as an examination of infectious disease and determination of blood groups using urine, blood serum, blood cells and blood plasma, comprising:
- a nozzle body hermetically mounted to seal an opening of said dilution cup using a packing, said nozzle body being detachable from said opening of said dilution cup;
- a cleaning water supply nozzle on said nozzle body for supplying cleaning water into the interior of said dilution cup;
- an air supply nozzle on said nozzle body for supplying air into the interior of said dilution cup by jetting the air into cleaning water in the dilution cup; and
- a discharging nozzle on said nozzle body for discharging cleaning water and air from the interior of said dilution cup.

2. The apparatus according to claim 1, further comprising a driving mechanism connected to said nozzle body, for moving said nozzle body up and down.

3. The apparatus according to claim 2, wherein said driving mechanism comprises a motor, a slidable cam moved by said motor, a vertically slidable plate having a bearing which contacts said cam, and a guide rod connected to said nozzle body, for transmitting driving forces of said vertically slidably plate in vertical directions.

4. The apparatus according to claim 1, wherein said opening of said cup is directed downward, and said cup has a bottom portion at a portion thereof opposite from said opening, and said discharging nozzle having a tip disposed at a bottom portion of said dilution cup.

5. The apparatus according to claim 1, wherein said opening of said dilution cup is directed upward, and a tip of said discharging nozzle and said air supply nozzle are at a bottom portion of said dilution cup.

* * * * *